US010517578B2

(12) United States Patent
Truckai

(10) Patent No.: US 10,517,578 B2
(45) Date of Patent: Dec. 31, 2019

(54) LAPAROSCOPIC DEVICE

(71) Applicant: Hermes Innovations, LLC, Cupertino, CA (US)

(72) Inventor: Csaba Truckai, Saratoga, CA (US)

(73) Assignee: Hermes Innovations LLC, Cupertino, CA (US)

( * ) Notice: Subject to any disclaimer, the term of this patent is extended or adjusted under 35 U.S.C. 154(b) by 162 days.

(21) Appl. No.: 15/488,270

(22) Filed: Apr. 14, 2017

(65) Prior Publication Data

US 2017/0215912 A1 Aug. 3, 2017

Related U.S. Application Data

(63) Continuation of application No. 14/508,856, filed on Oct. 7, 2014, now Pat. No. 9,649,125.

(Continued)

(51) Int. Cl.

*A61B 17/22* (2006.01)
*A61B 17/32* (2006.01)

(Continued)

(52) U.S. Cl.

CPC .. *A61B 17/00234* (2013.01); *A61B 17/32002* (2013.01); *A61B 17/320068* (2013.01); *A61B 17/3203* (2013.01); *A61B 2017/00022* (2013.01); *A61B 2017/00026* (2013.01); *A61B 2017/00039* (2013.01); *A61B 2017/00477* (2013.01); *A61B 2017/00973* (2013.01);

(Continued)

(58) Field of Classification Search

CPC ...... A61B 17/32002; A61B 17/320068; A61B 2017/320028; A61B 2017/22027; A61B 2017/22079

See application file for complete search history.

(56) References Cited

U.S. PATENT DOCUMENTS 3,903,891 A 9/1975 Brayshaw
4,428,748 A 1/1984 Peyman et al.

(Continued)

FOREIGN PATENT DOCUMENTS

CN 1977194 A 6/2007
CN 101015474 A 8/2007

(Continued)

OTHER PUBLICATIONS

European search report and search opinion dated Apr. 16, 2013 for EP Application No. 09822443.

(Continued)

*Primary Examiner* — Julian W Woo

(74) *Attorney, Agent, or Firm* — Wilson Sonsini Goodrich & Rosati

(57) ABSTRACT

A medical instrument includes a tubular cutter extending along an axis and having a windowed outer sleeve and a moveable inner cutting sleeve. An ultrasound transducer is operatively coupled to the inner cutting sleeve in order to induce motion in the inner cutting sleeve to enhance cutting or resection of tissue by the inner cutting sleeve as it is reciprocated or otherwise moved past the cutting window. The instrument typically will include a motor drive configured to reciprocate and/or rotate the inner cutting sleeve relative to the windowed outer sleeve, usually at a reciprocation rate between 1 and 10 Hz.

28 Claims, 11 Drawing Sheets

500
525
515
544
540
512
545
518
565
568
570a
570b
562
552
555
FLUID SOURCE 260
CONTROLLER 210
NEGATIVE PRESSURE SOURCE 240

Related U.S. Application Data

(60) Provisional application No. 61/891,288, filed on Oct. 15, 2013.

(51) Int. Cl.
*A61B 17/00* (2006.01)
*A61B 17/3203* (2006.01)
*A61B 90/00* (2016.01)

(52) U.S. Cl.
CPC ............... *A61B 2017/22027* (2013.01); *A61B 2017/22079* (2013.01); *A61B 2017/32007* (2017.08); *A61B 2017/320028* (2013.01); *A61B 2090/065* (2016.02); *A61B 2217/005* (2013.01)

(56) References Cited

U.S. PATENT DOCUMENTS 4,949,718 A 8/1990 Neuwirth et al.
4,979,948 A 12/1990 Geddes et al.
4,989,583 A * 2/1991 Hood ............. A61B 17/320068 601/2
5,045,056 A 9/1991 Behl
5,078,717 A 1/1992 Parins et al.
5,084,044 A 1/1992 Quint
5,191,883 A 3/1993 Lennox et al.
5,197,963 A 3/1993 Parins
5,242,390 A 9/1993 Goldrath
5,248,312 A 9/1993 Langberg
5,277,201 A 1/1994 Stern
5,282,799 A 2/1994 Rydell
5,324,254 A 6/1994 Phillips
5,344,435 A 9/1994 Turner et al.
5,374,261 A 12/1994 Yoon
5,401,272 A 3/1995 Perkins
5,401,274 A 3/1995 Kusunoki
5,429,136 A 7/1995 Milo et al.
5,441,498 A 8/1995 Perkins
5,443,470 A 8/1995 Stern et al.
5,456,689 A 10/1995 Kresch et al.
5,496,314 A 3/1996 Eggers
5,501,681 A 3/1996 Neuwirth et al.
5,505,730 A 4/1996 Edwards
5,507,725 A 4/1996 Savage et al.
5,558,672 A 9/1996 Edwards et al.
5,562,703 A 10/1996 Desai
5,562,720 A 10/1996 Stern et al.
5,575,788 A 11/1996 Baker et al.
5,584,872 A 12/1996 LaFontaine et al.
5,622,647 A 4/1997 Kerr et al.
5,647,848 A 7/1997 Jorgensen
5,653,684 A 8/1997 Laptewicz et al.
5,653,692 A 8/1997 Masterson et al.
5,662,647 A 9/1997 Crow et al.
5,672,174 A 9/1997 Gough et al.
5,681,308 A 10/1997 Edwards et al.
5,697,281 A 12/1997 Eggers et al.
5,697,882 A 12/1997 Eggers et al.
5,713,942 A 2/1998 Stern et al.
5,733,298 A 3/1998 Berman et al.
5,769,846 A 6/1998 Edwards et al.
5,769,880 A 6/1998 Truckai et al.
5,779,662 A 7/1998 Berman
5,800,493 A 9/1998 Stevens et al.
5,810,802 A 9/1998 Panescu et al.
5,827,273 A 10/1998 Edwards
5,843,020 A 12/1998 Tu et al.
5,846,239 A 12/1998 Swanson et al.
5,860,974 A 1/1999 Abele
5,876,340 A 3/1999 Tu et al.
5,879,347 A 3/1999 Saadat
5,891,094 A 4/1999 Masterson et al.
5,891,134 A 4/1999 Goble et al.
5,891,136 A 4/1999 McGee et al.
5,902,251 A 5/1999 Vanhooydonk
5,904,651 A 5/1999 Swanson et al.
5,925,038 A 7/1999 Panescu et al.
5,954,714 A 9/1999 Saadat et al.
5,964,755 A 10/1999 Edwards
5,976,129 A 11/1999 Desai
5,980,515 A 11/1999 Tu
5,997,534 A 12/1999 Tu et al.
6,024,743 A 2/2000 Edwards
6,026,331 A 2/2000 Feldberg et al.
6,041,260 A 3/2000 Stern et al.
6,053,909 A 4/2000 Shadduck
6,057,689 A 5/2000 Saadat
6,086,581 A 7/2000 Reynolds et al.
6,113,597 A 9/2000 Eggers et al.
6,139,570 A 10/2000 Saadat et al.
6,146,378 A 11/2000 Mikus et al.
6,149,620 A 11/2000 Baker et al.
6,214,003 B1 4/2001 Morgan et al.
6,228,078 B1 5/2001 Eggers et al.
6,254,599 B1 7/2001 Lesh et al.
6,283,962 B1 9/2001 Tu et al.
6,296,639 B1 10/2001 Truckai et al.
6,302,904 B1 10/2001 Wallstén et al.
6,315,776 B1 11/2001 Edwards et al.
6,366,818 B1 4/2002 Bolmsjo
6,387,088 B1 5/2002 Shattuck et al.
6,395,012 B1 5/2002 Yoon et al.
6,409,722 B1 6/2002 Hoey et al.
6,416,508 B1 7/2002 Eggers et al.
6,416,511 B1 7/2002 Lesh et al.
6,443,947 B1 9/2002 Marko et al.
6,491,690 B1 12/2002 Goble et al.
6,508,815 B1 1/2003 Strul et al.
6,551,310 B1 4/2003 Ganz et al.
6,565,561 B1 5/2003 Goble et al.
6,589,237 B2 7/2003 Woloszko et al.
6,602,248 B1 8/2003 Sharps et al.
6,607,545 B2 8/2003 Kammerer et al.
6,622,731 B2 9/2003 Daniel et al.
6,635,054 B2 10/2003 Fjield et al.
6,635,055 B1 10/2003 Cronin
6,663,626 B2 12/2003 Truckai et al.
6,673,071 B2 1/2004 Vandusseldorp et al.
6,699,241 B2 3/2004 Rappaport et al.
6,726,684 B1 4/2004 Woloszko et al.
6,736,811 B2 5/2004 Panescu et al.
6,746,447 B2 6/2004 Davison et al.
6,758,847 B2 7/2004 Maguire
6,780,178 B2 8/2004 Palanker et al.
6,802,839 B2 10/2004 Behl
6,813,520 B2 11/2004 Truckai et al.
6,814,730 B2 11/2004 Li
6,832,996 B2 12/2004 Woloszko et al.
6,837,887 B2 1/2005 Woloszko et al.
6,837,888 B2 1/2005 Ciarrocca et al.
6,840,935 B2 1/2005 Lee
6,872,205 B2 3/2005 Lesh et al.
6,896,674 B1 5/2005 Woloszko et al.
6,905,497 B2 6/2005 Truckai et al.
6,923,805 B1 8/2005 LaFontaine et al.
6,929,642 B2 8/2005 Xiao et al.
6,949,096 B2 9/2005 Davison et al.
6,951,569 B2 10/2005 Nohilly et al.
6,954,977 B2 10/2005 Maguire et al.
6,960,203 B2 11/2005 Xiao et al.
7,074,217 B2 7/2006 Strul et al.
7,083,614 B2 8/2006 Fjield et al.
7,087,052 B2 8/2006 Sampson et al.
7,108,696 B2 9/2006 Daniel et al.
7,118,590 B1 10/2006 Cronin
7,150,747 B1 12/2006 McDonald et al.
7,175,734 B2 2/2007 Stewart et al.
7,179,255 B2 2/2007 Lettice et al.
7,186,234 B2 3/2007 Dahla et al.
7,192,430 B2 3/2007 Truckai et al.
7,238,185 B2 7/2007 Palanker et al.
7,270,658 B2 9/2007 Woloszko et al.
7,276,063 B2 10/2007 Davison et al.

(56) References Cited

U.S. PATENT DOCUMENTS 7,278,994 B2 10/2007 Goble
7,294,126 B2 11/2007 Sampson et al.
7,297,143 B2 11/2007 Woloszko et al.
7,326,201 B2 2/2008 Fjield et al.
7,331,957 B2 2/2008 Woloszko et al.
RE40,156 E 3/2008 Sharps et al.
7,371,231 B2 5/2008 Rioux et al.
7,371,235 B2 5/2008 Thompson et al.
7,381,208 B2 6/2008 Van Der Walt et al.
7,387,628 B1 6/2008 Behl et al.
7,407,502 B2 8/2008 Strul et al.
7,419,500 B2 9/2008 Marko et al.
7,452,358 B2 11/2008 Stern et al.
7,462,178 B2 12/2008 Woloszko et al.
7,500,973 B2 3/2009 Vancelette et al.
7,512,445 B2 3/2009 Truckai et al.
7,530,979 B2 5/2009 Ganz et al.
7,549,987 B2 6/2009 Shadduck
7,556,628 B2 7/2009 Utley et al.
7,566,333 B2 7/2009 Van Wyk et al.
7,572,251 B1 8/2009 Davison et al.
7,604,633 B2 10/2009 Truckai et al.
7,625,368 B2 12/2009 Schechter et al.
7,674,259 B2 3/2010 Shadduck
7,678,106 B2 3/2010 Lee
7,708,733 B2 5/2010 Sanders et al.
7,717,909 B2 5/2010 Strul et al.
7,736,362 B2 6/2010 Eberl et al.
7,749,159 B2 7/2010 Crowley et al.
7,824,398 B2 11/2010 Woloszko et al.
7,824,405 B2 11/2010 Woloszko et al.
7,846,160 B2 12/2010 Payne et al.
7,879,034 B2 2/2011 Woloszko et al.
7,918,795 B2 4/2011 Grossman
7,985,188 B2 7/2011 Felts et al.
8,016,843 B2 * 9/2011 Escaf .................. A61F 9/00745 606/166
8,197,476 B2 6/2012 Truckai
8,197,477 B2 6/2012 Truckai
8,372,068 B2 2/2013 Truckai
8,382,753 B2 2/2013 Truckai
8,486,096 B2 7/2013 Robertson et al.
8,500,732 B2 8/2013 Truckai et al.
8,540,708 B2 9/2013 Truckai et al.
8,690,873 B2 4/2014 Truckai et al.
8,728,003 B2 * 5/2014 Taylor ................ A61B 10/0275 600/564
8,821,486 B2 9/2014 Toth et al.
8,998,901 B2 4/2015 Truckai et al.
9,427,249 B2 * 8/2016 Robertson ........ A61B 17/22004
9,510,897 B2 12/2016 Truckai et al.
9,649,125 B2 5/2017 Truckai
9,662,163 B2 5/2017 Toth et al.
9,999,466 B2 * 6/2018 Germain ............ A61B 18/1206
2002/0022870 A1 2/2002 Truckai et al.
2002/0058933 A1 5/2002 Christopherson et al.
2002/0068934 A1 6/2002 Edwards et al.
2002/0082635 A1 6/2002 Kammerer et al.
2002/0183742 A1 12/2002 Carmel et al.
2003/0065321 A1 4/2003 Carmel et al.
2003/0130655 A1 7/2003 Woloszko et al.
2003/0153905 A1 8/2003 Edwards et al.
2003/0171743 A1 9/2003 Tasto et al.
2003/0176816 A1 9/2003 Maguire et al.
2003/0208200 A1 11/2003 Palanker et al.
2003/0216725 A1 11/2003 Woloszko et al.
2004/0002702 A1 1/2004 Xiao et al.
2004/0010249 A1 1/2004 Truckai et al.
2004/0087936 A1 5/2004 Stern et al.
2004/0092980 A1 5/2004 Cesarini et al.
2004/0102770 A1 5/2004 Goble
2004/0215180 A1 10/2004 Starkebaum et al.
2004/0215182 A1 10/2004 Lee
2004/0215296 A1 10/2004 Ganz et al.
2004/0230190 A1 11/2004 Dahla et al.
2005/0075630 A1 4/2005 Truckai et al.
2005/0165389 A1 7/2005 Swain et al.
2005/0182397 A1 8/2005 Ryan
2005/0192652 A1 9/2005 Cioanta et al.
2005/0228372 A1 10/2005 Truckai et al.
2005/0240176 A1 10/2005 Oral et al.
2005/0251131 A1 11/2005 Lesh
2006/0009756 A1 1/2006 Francischelli et al.
2006/0052771 A1 3/2006 Sartor et al.
2006/0084969 A1 4/2006 Truckai et al.
2006/0089637 A1 4/2006 Werneth et al.
2006/0178670 A1 8/2006 Woloszko et al.
2006/0189971 A1 8/2006 Tasto et al.
2006/0189976 A1 8/2006 Karni et al.
2006/0224154 A1 10/2006 Shadduck et al.
2006/0259025 A1 11/2006 Dahla
2007/0021743 A1 1/2007 Rioux et al.
2007/0083192 A1 4/2007 Welch
2007/0161981 A1 7/2007 Sanders et al.
2007/0213704 A1 9/2007 Truckai et al.
2007/0282323 A1 12/2007 Woloszko et al.
2007/0287996 A1 12/2007 Rioux
2007/0288075 A1 12/2007 Dowlatshahi
2007/0293853 A1 12/2007 Truckai et al.
2008/0058797 A1 3/2008 Rioux
2008/0097242 A1 4/2008 Cai
2008/0097425 A1 4/2008 Truckai
2008/0125765 A1 5/2008 Berenshteyn et al.
2008/0125770 A1 5/2008 Kleyman
2008/0154238 A1 6/2008 McGuckin
2008/0183132 A1 7/2008 Davies et al.
2008/0208189 A1 8/2008 Van Wyk et al.
2008/0221567 A1 9/2008 Sixto et al.
2008/0249518 A1 10/2008 Warnking et al.
2008/0249533 A1 10/2008 Godin
2008/0281317 A1 11/2008 Gobel
2009/0048593 A1 2/2009 Ganz et al.
2009/0054888 A1 2/2009 Cronin
2009/0054892 A1 2/2009 Rioux et al.
2009/0076494 A1 3/2009 Azure
2009/0105703 A1 4/2009 Shadduck
2009/0131927 A1 5/2009 Kastelein et al.
2009/0149846 A1 6/2009 Hoey et al.
2009/0163908 A1 6/2009 MacLean et al.
2009/0209956 A1 8/2009 Marion
2009/0306654 A1 12/2009 Garbagnati
2010/0004595 A1 1/2010 Nguyen et al.
2010/0036372 A1 2/2010 Truckai et al.
2010/0042095 A1 2/2010 Bigley et al.
2010/0042097 A1 2/2010 Newton et al.
2010/0049190 A1 2/2010 Long et al.
2010/0100091 A1 4/2010 Truckai
2010/0100094 A1 4/2010 Truckai
2010/0106152 A1 4/2010 Truckai et al.
2010/0114089 A1 5/2010 Truckai et al.
2010/0121319 A1 5/2010 Chu et al.
2010/0125269 A1 5/2010 Emmons et al.
2010/0137855 A1 6/2010 Berjano Zanon et al.
2010/0137857 A1 6/2010 Shroff et al.
2010/0152725 A1 6/2010 Pearson et al.
2010/0185191 A1 7/2010 Carr et al.
2010/0198214 A1 8/2010 Layton, Jr. et al.
2010/0204688 A1 8/2010 Hoey et al.
2010/0217256 A1 8/2010 Strul et al.
2010/0228239 A1 9/2010 Freed
2010/0228245 A1 9/2010 Sampson et al.
2010/0286680 A1 11/2010 Kleyman
2011/0004205 A1 1/2011 Chu et al.
2011/0060391 A1 3/2011 Unetich et al.
2011/0112524 A1 5/2011 Stern et al.
2011/0196401 A1 8/2011 Robertson et al.
2011/0196403 A1 * 8/2011 Robertson ...... A61B 17/320068 606/169
2011/0282340 A1 11/2011 Toth et al.
2012/0041434 A1 2/2012 Truckai
2012/0041437 A1 2/2012 Truckai
2012/0330292 A1 12/2012 Shadduck et al.
2013/0172870 A1 7/2013 Germain et al.
2013/0231652 A1 9/2013 Germain et al.

(56) References Cited

U.S. PATENT DOCUMENTS

| | | | |
|---|---|---|---|
| 2013/0267937 | A1 | 10/2013 | Shadduck et al. |
| 2013/0296847 | A1 | 11/2013 | Germain et al. |
| 2013/0331833 | A1 | 12/2013 | Bloom |
| 2013/0345705 | A1 | 12/2013 | Truckai et al. |
| 2014/0012249 | A1 | 1/2014 | Truckai et al. |
| 2014/0303611 | A1 | 10/2014 | Shadduck et al. |
| 2014/0336632 | A1 | 11/2014 | Toth et al. |
| 2015/0119916 | A1 | 4/2015 | Dietz et al. |
| 2015/0173827 | A1 | 6/2015 | Bloom et al. |
| 2015/0182281 | A1 | 7/2015 | Truckai et al. |
| 2016/0095615 | A1 | 4/2016 | Orczy-Timko et al. |
| 2016/0242844 | A1 | 8/2016 | Orczy-Timko |

FOREIGN PATENT DOCUMENTS

| | | | |
|---|---|---|---|
| CN | 101198288 | A | 6/2008 |
| EP | 1236440 | A1 | 9/2002 |
| EP | 1595507 | A2 | 11/2005 |
| EP | 2349044 | A1 | 8/2011 |
| EP | 2493407 | A1 | 9/2012 |
| JP | 2005501597 | A | 1/2005 |
| WO | WO-0053112 | A2 | 9/2000 |
| WO | WO-2005122938 | A1 | 12/2005 |
| WO | WO-2006001455 | A1 | 1/2006 |
| WO | WO-2008083407 | A1 | 7/2008 |
| WO | WO-2010048007 | A1 | 4/2010 |
| WO | WO-2011053599 | A1 | 5/2011 |
| WO | WO-2011060301 | A1 | 5/2011 |
| WO | WO-2014165715 | A1 | 10/2014 |

OTHER PUBLICATIONS

European search report and search opinion dated Jul. 10, 2013 for EP Application No. 10827399.
International search report and written opinion dated Feb. 2, 2011 for PCT/US2010/056591.
International Search Report and Written Opinion dated May 31, 2017 for International PCT Patent Application No. PCT/US2017/014456.
International search report and written opinion dated Dec. 10, 2009 for PCT/US2009/060703.
International search report and written opinion dated Dec. 14, 2010 for PCT/US2010/054150.
International Search Report dated Jul. 6, 2016 for PCT/US16/25509.
International Search Report dated Sep. 10, 2014 for PCT/US2014/032895.
Notice of allowance dated Jan. 9, 2014 for U.S. Appl. No. 13/938,032.
Notice of Allowance dated Jan. 27, 2017 for U.S. Appl. No. 13/236,471.
Notice of Allowance dated Jan. 27, 2017 for U.S. Appl. No. 14/508,856.
Notice of allowance dated Feb. 25, 2015 for U.S. Appl. No. 13/975,139.
Notice of allowance dated Mar. 5, 2012 for U.S. Appl. No. 13/281,846.
Notice of allowance dated Mar. 5, 2012 for U.S. Appl. No. 13/281,856.
Notice of allowance dated Mar. 29, 2013 for U.S. Appl. No. 12/605,546.
Notice of allowance dated May 9, 2014 for U.S. Appl. No. 12/944,466.
Notice of allowance dated May 24, 2013 for U.S. Appl. No. 12/605,929.
Notice of Allowance dated Aug. 2, 2016 for U.S. Appl. No. 13/281,805.
Notice of allowance dated Nov. 15, 2012 for U.S. Appl. No. 12/541,043.
Notice of allowance dated Nov. 15, 2012 for U.S. Appl. No. 12/541,050.
Notice of allowance dated Dec. 2, 2014 for U.S. Appl. No. 13/975,139.
Office action dated Jan. 28, 2013 for U.S. Appl. No. 12/605,546.
Office action dated Feb. 4, 2016 for U.S. Appl. No. 13/857,068.
Office Action dated Mar. 9, 2017 for U.S. Appl. No. 15/091,402.
Office action dated Mar. 12, 2012 for U.S. Appl. No. 12/541,043.
Office action dated Mar. 12, 2012 for U.S. Appl. No. 12/541,050.
Office Action dated Mar. 14, 2017 for U.S. Appl. No. 15/410,723.
Office Action dated Mar. 31, 2016 for U.S. Appl. No. 13/281,805.
Office Action dated Apr. 5, 2017 for U.S. Appl. No. 13/857,068.
Office Action dated Apr. 18, 2017 for U.S. Appl. No. 14/657,684.
Office Action dated Apr. 22, 2016 for U.S. Appl. No. 14/657,684.
Office action dated Apr. 24, 2014 for U.S. Appl. No. 13/975,139.
Office Action dated May 9, 2017 for U.S. Appl. No. 15/410,723.
Office action dated May 22, 2015 for U.S. Appl. No. 14/657,684.
Office action dated Jun. 5, 2015 for U.S. Appl. No. 13/857,068.
Office action dated Jun. 18, 2012 for U.S. Appl. No. 12/605,546.
Office Action dated Jun. 29, 2016 for U.S. Appl. No. 14/508,856.
Office Action dated Jul. 5, 2016 for U.S. Appl. No. 13/236,471.
Office action dated Jul. 23, 2015 for U.S. Appl. No. 13/281,805.
Office Action dated Sep. 7, 2016 for U.S. Appl. No. 13/857,068.
Office action dated Sep. 22, 2014 for U.S. Appl. No. 13/281,805.
Office action dated Sep. 24, 2015 for U.S. Appl. No. 13/236,471.
Office action dated Sep. 28, 2012 for U.S. Appl. No. 12/541,043.
Office action dated Sep. 28, 2012 for U.S. Appl. No. 12/541,050.
Office action dated Sep. 28, 2012 for U.S. Appl. No. 12/605,929.
Office Action dated Sep. 30, 2016 for U.S. Appl. No. 15/091,402.
Office action dated Oct. 9, 2014 for U.S. Appl. No. 13/857,068.
Office action dated Oct. 24, 2014 for U.S. Appl. No. 13/975,139.
Office Action dated Nov. 2, 2016 for U.S. Appl. No. 14/657,684.
Office action dated Nov. 6, 2013 for U.S. Appl. No. 13/938,032.
Office action dated Dec. 4, 2014 for U.S. Appl. No. 13/236,471.
Office action dated Dec. 6, 2011 for U.S. Appl. No. 13/281,846.
Office action dated Dec. 16, 2014 for U.S. Appl. No. 13/281,805.
Office action dated Dec. 22, 2011 for U.S. Appl. No. 13/281,856.

* cited by examiner

LAPAROSCOPIC DEVICE

CROSS-REFERENCE TO RELATED APPLICATIONS

This application is a continuation of U.S. patent application Ser. No. 14/508,856, filed Oct. 7, 2014, now U.S. Pat. No. 9,649,125, which claims the benefit of U.S. Provisional Application No. 61/891,288, filed Oct. 15, 2013, the entire content of which is incorporated herein by reference.

BACKGROUND OF THE INVENTION

1. Field of the Invention

The present invention relates devices and methods for cutting and removal of tissue from the interior of a patient's body, typically in a laparosopic procedure.

Laparoscopic and other minimally invasive tissue cutters are known, some of which operate by advancing a tubular blade past an open window in an outer housing to resect or sever intruding tissue. Optionally the cutter may be rotated as it is axially advanced past the window to enhance cutting. Although quite effective, such cutters cannot always adequately cut difficult tissue structure, and it would therefore be advantageous to provide improved devices and methods for laparoscopic and other minimally invasive tissue resection, 2. Description of the Background Art Reciprocating and rotational tissue cutters are described in U.S. Published Patent Applications 20130267937; 20130172870; and 20120330292. Atherectomy catheters having ultrasound imaging transducers on the cutting blades are described in U.S. Pat. No. 5,429,136.

SUMMARY OF THE INVENTION

In a first aspect, the present invention provides a medical instrument comprising a tubular cutter extending along an axis and having a windowed outer sleeve and a moveable inner cutting sleeve. An ultrasound transducer is operatively coupled to the inner cutting sleeve in order to induce motion in the inner cutting sleeve to enhance cutting or resection of tissue by the inner cutting sleeve as it is reciprocated or otherwise moved past the cutting window. The instrument typically will include a motor drive configured to reciprocate and/or rotate the inner cutting sleeve relative to the windowed outer sleeve, usually at a reciprocation rate between 1 and 10 Hz.

The ultrasound transducer is typically configured to cause at least one of axial motion and rotational motion in the distal end of the inner cutting sleeve. Usually, the inner cutting sleeve will have a cutting edge at is distal end so that the tissue may be effected by axially advancing the blade in a distal direction. Rotational and/or oscillatory motion may be superimposed on the axial reciprocation to enhance cutting with the ultrasonic motion being further superimposed to further enhance cutting. In other embodiments, the inner cutting sleeve may have an axially oriented cutting edge so that cutting is provided primarily by rotation of the sleeve about the axis. In that case, axial oscillation may be superimposed to enhance cutting together with the ultrasonic motion. In all cases, a dimension between the ultrasound transducer and the distal end of the inner sleeve may be selected to optimize at least one of axial motion and rotational motion in the distal end of the inner cutting sleeve.

In some embodiments, the instrument may further comprise at least a second ultrasound transducer, wherein first and second ultrasound transducers are configured to cause axial and rotational motion in the distal end of the inner sleeve. The ultrasound transducer may be removably secured to a handle portion of the tubular cutter.

The instruments of the present invention may further comprise a negative pressure source coupled to a tissue extraction lumen in the tubular cutter. The instrument of the present invention may still further comprise a pressurized fluid source, either liquid, gas, or a mixed fluid, coupled to an inflow lumen in the cutter, and the inflow lumen may extend to an outlet in a distal portion of the cutter.

The instruments of the present invention may further comprise a controller coupled to the tubular cutter for controlling operating parameters of the ultrasound transducer, the motor drive, the negative pressure source, and/or the pressurized fluid source. In such cases, the instruments may still further comprise a sensor configured to send signals to the controller indicating the position of the inner sleeve relative to the window in the outer sleeve, and the controller may be adapted or configured to modulate activation of the ultrasound transducer in response to the sensor signals that indicate the position of the inner sleeve. The controller may activate the ultrasound transducer when the inner sleeve moves toward a window-closed position to cut tissue and de-activates the ultrasound transducer when the inner sleeve moves toward a window-open position. In particular, the controller may activate the pressurized fluid source when the inner sleeve is in a window-closed position and/or may de-activate the pressurized fluid source when the inner sleeve is in a window-open position.

In a second aspect, the present invention provides a medical instrument comprising a tubular assembly extending along an axis with a windowed outer sleeve and a moveable inner cutting sleeve. The inner cutting sleeve has a tissue-extraction passageway. A seal in the tissue-extraction passageway in the inner cutting sleeve has a first condition that closes the passageway and second condition that permits a tissue chip to pass through the seal. The tubular assembly typically has a flow channel terminating in a distal outlet in a region of the assembly that is distal to the seal, where the flow channel is in communication with a fluid source or a negative pressure source.

DETAILED DESCRIPTION OF THE INVENTION

Figure 1:
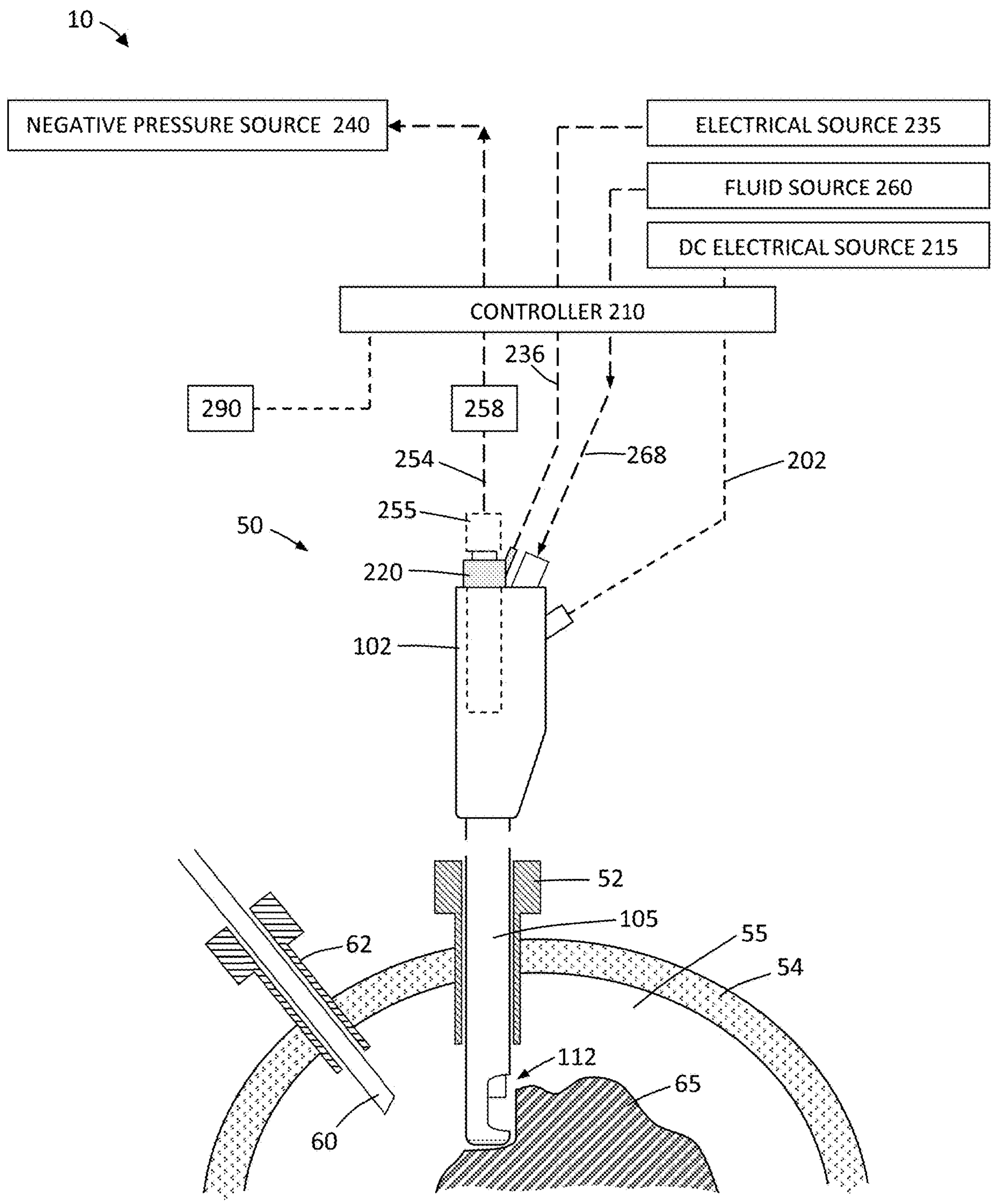
FIG. 1 is a schematic view of a tissue resecting device and block diagram of operating components corresponding to the invention in a laparoscopic resection procedure.
Figure 2A:
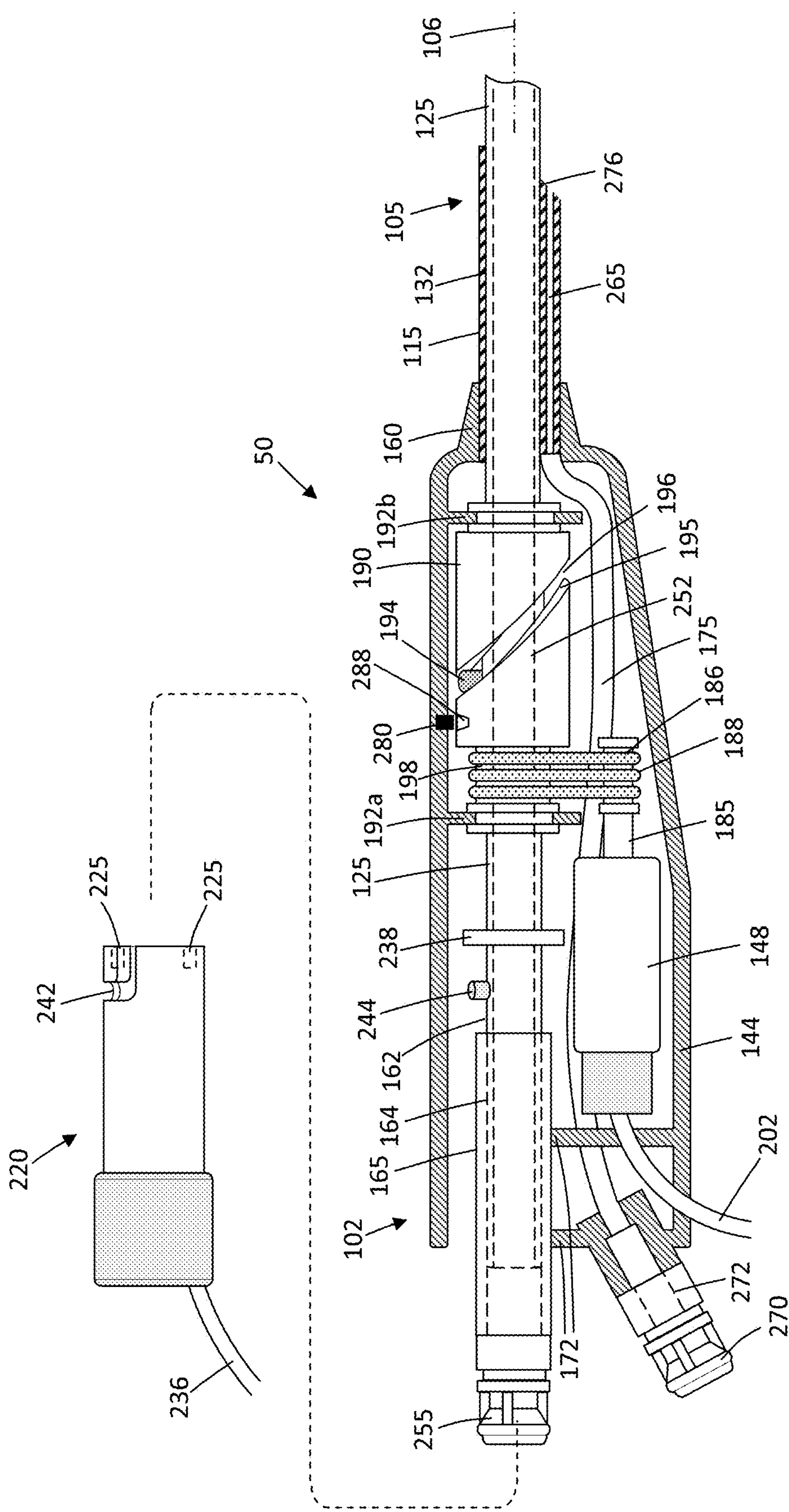
FIG. 2A is a cut-away view of a handle portion of a resecting device of the invention with a detachable ultrasound component de-coupled from the device.
Figure 2B:
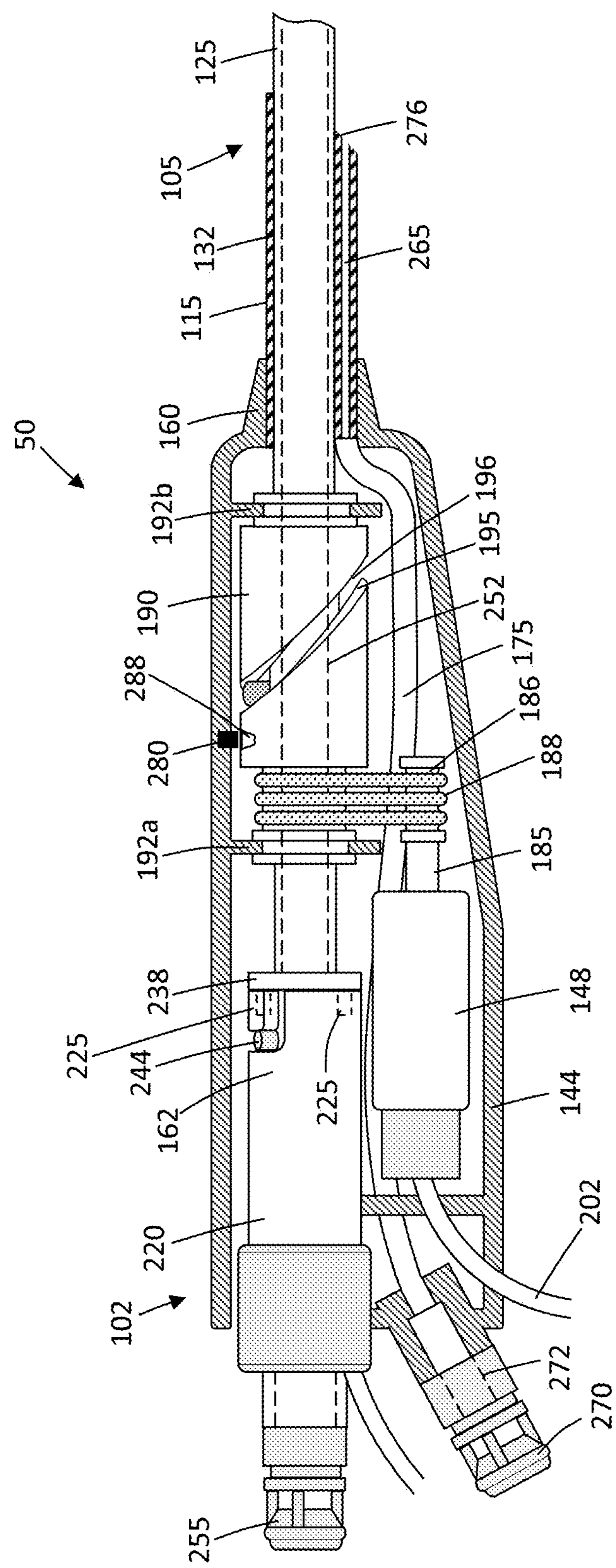
FIG. 2B is a cut-away view of the resecting device handle as in FIG. 2A with the ultrasound component coupled to the resecting device to provide vibratory motion to the inner sleeve.

FIGS. 1, and 2A-2B illustrate a tissue resecting system 10 that includes a hand-held single-use tissue resection device 50. The device 50 has a handle portion 102 that is coupled to a shaft portion 105 having an outer diameter ranging from about 3 mm to 20 mm. The shaft portion 105 extends along axis 106 and can have a length suitable for introducing directly into a body space, for introducing though a trocar in a laparoscopic procedure or for introducing through a working channel of an endoscope. A hand-held device corresponding to the invention as depicted in FIGS. 1 and 2A-2B is adapted for laparoscopic resection procedures such as in a hysterectomy. FIG. 1 schematically illustrates the tissue resecting device 50 introduced through a trocar sleeve or port 52 in a body wall 54 to an insufflated working space 55, which, for example, can be an abdominal cavity. An endoscope 60 is introduced through a second port 62 to allow viewing of the tissue volume 65 targeted for resection and extraction. An additional port can be provided for a tissue grasping instrument (not shown) that may be used in the resection procedure. In another embodiment, a similar elongate resecting device can be configured for resecting tissue in other body tracts and spaces utilizing any type of endoscope to allow endoscopic viewing of the working space.

Referring to FIGS. 1, 2A-2B and 3, the resecting device 50 has a shaft portion 105 and working end 112 that comprises an assembly of a first or outer sleeve 115 extending along axis 106 to a distal end 116 having a window 118 therein for receiving tissue. A second or inner sleeve 125 with a distal blade edge 126 and distal opening 128 is dimensioned to reciprocate in bore 132 of outer sleeve 115. The outer and inner sleeves, 115 and 125, are typically fabricated of thin-wall stainless steel but any other suitable materials can be used. As can be understood from FIG. 4, reciprocation of the inner sleeve 125 will cut tissue captured in the window 118 of the outer sleeve. FIG. 4 shows the working end 112 or the assembly of outer sleeve 115 and inner sleeve 125 with the inner sleeve in a partially window-open position.

The resecting device 50 of FIGS. 1-2B includes subsystems operatively coupled to handle 102 and inner sleeve 125 to enhance the cutting and removal of tissue from a working space in the interior of a patient's body. FIG. 2A is a cut-away view of handle 102 of the resecting device showing outer sleeve 115 fixed to collar portion 160 of the handle. The handle 102 typically consists of a molded plastic two-part handle shell with a hollow interior. In one variation shown in FIGS. 1 and 2A, the reciprocatable inner sleeve 125 extends partly through the interior of handle 102 and has a proximal sleeve end 162 that is received in bore 164 of cylindrical fixed member 165 that is fixed to support brackets 172 in shell 144 of handle 102. As will be described below, the inner sleeve 125 is reciprocated by DC electrical motor 148 in handle portion 102 (see FIGS. 2A-2B).

In one embodiment, the DC motor 148 is housed within the handle with motor shaft 185 having a pulley 186 that carries one or more flexible belts 188. The belts 188 can be fabricated of rubber, Viton® or a similar material and are adapted to rotate the cylindrical drive member 190 which in turn converts rotational motion to axial motion to thereby reciprocate the inner sleeve 125. A gear system instead of belts 188 also can be used to rotate the drive member 190. The drive member 190 is rotatable and secured in the handle 102 at rotation-permitting collars 192*a* and 192*b* at ends of the drive member. The inner sleeve 125 extends through the drive member 190 and has a projecting first pin 194 that engages the inner surfaces 195 of arcuate slot 196 in drive member 190. The DC motor is geared (together with pulleys 186 and 198) to rotate the drive member 190 at suitable speed to reciprocate the inner sleeve 125 within a range of 1 Hz to 10 Hz. The DC motor 148 has an electrical cable 202 extending to the controller 210 and a DC electrical source 215.

Figure 3:
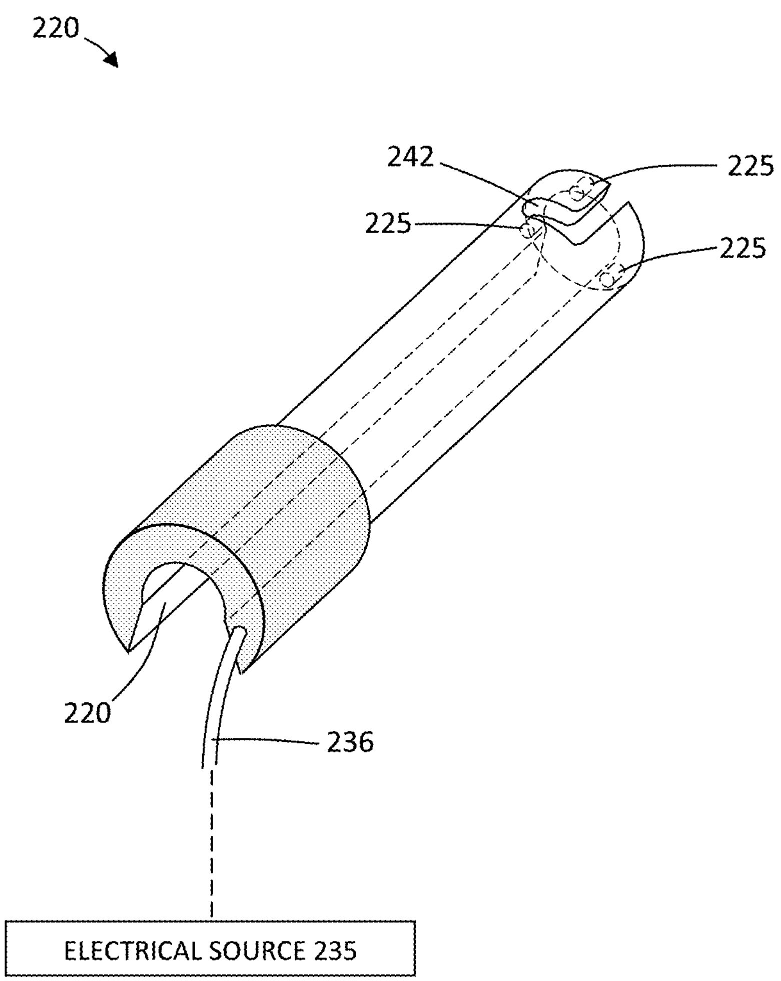
FIG. 3 is a perspective view of the ultrasound component de-coupled from the resecting device illustrating a plurality of piezoelectric elements carried therein.
Figure 4:
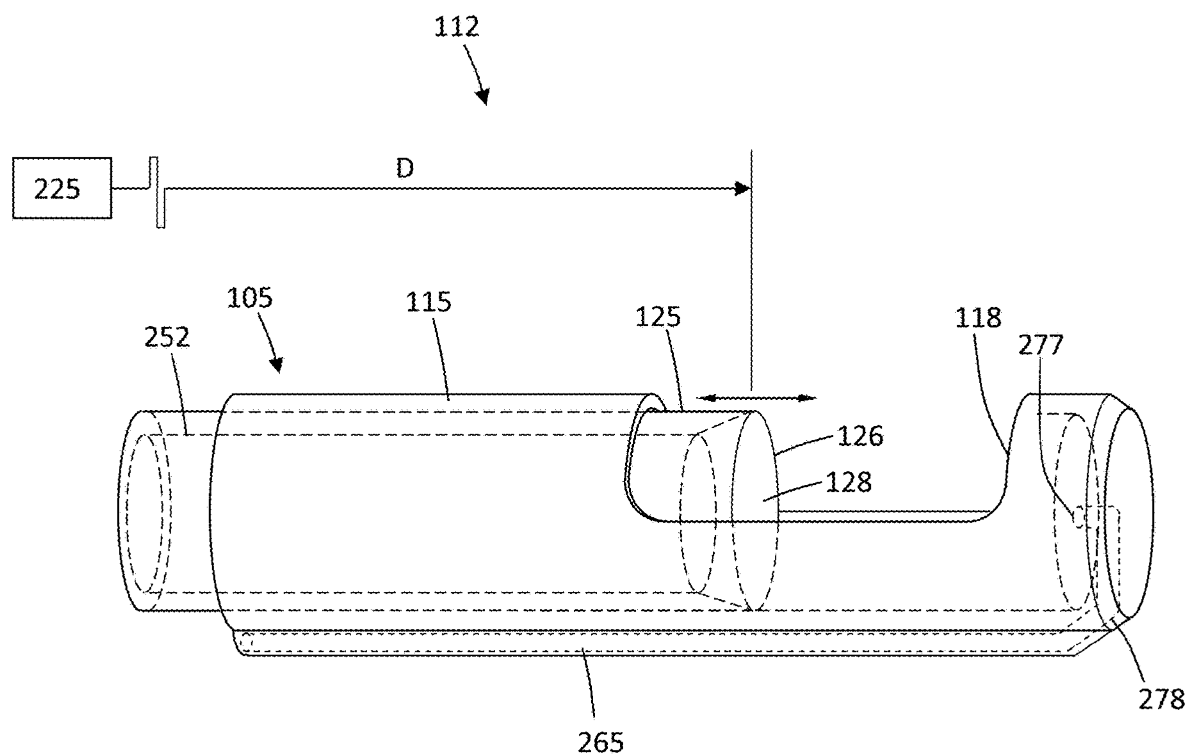
FIG. 4 is a perspective view of the working end of a shaft portion of the resecting device showing the assembly of the outer and inner sleeves.

Referring to FIGS. 2A, 2B and 3, the resecting device 10 may be part of a system that includes a vibratory or ultrasound component 220 that is re-useable and removable from the resecting device 50. As can be seen in FIG. 3, the ultrasound component 220 has an elongate slot 222 therein that is configured to allow the component to slide axially over cylindrical fixed member 165 and the inner sleeve 125. Component 220 carries a vibrating mechanism such as at least one piezoelectric element 225 for applying vibratory motion to the inner sleeve 125 and more particularly to the distal blade edge 126 of the inner sleeve 125. In one variation shown in FIGS. 2A-3, three piezoelectric elements 225 are shown. An electrical source 235 is coupled to the piezoelectric elements 225 (see FIGS. 1 and 3) through electrical cable 236 and electrical leads (not shown) in the ultrasound component 220 to drive the piezoelectric elements. As can be seen in FIGS. 2A-3, the ultrasound component 220 has a J-lock 242 that engages second pin 244 of the inner sleeve 125 for securely locking the component 220 to the inner sleeve. The piezoelectric elements 225 are locked to inner sleeve 125 and are adapted to transmit energy to flange 238 of inner sleeve 125 and to its distal blade edge 126 (see FIGS. 2A-2B and 4). In one variation, the dimension between the piezoelectric element 225 and the distal blade edge 126 (see FIG. 4) of inner sleeve 125 is selected to optimize motion in the blade edge. The dimension D relates to the length of a standing wave caused by the piezoelectric element in the material of sleeve 125 as is known in that art of utilizing ultrasound to activate the working end of medical instruments. It should be appreciated that any suitable locking feature can be used to detachably couple the ultrasound component 220 to the inner sleeve 125 such as a threaded connector, a clamp, catches, magnets or the like. It should further be appreciated that independent electrical cable 236 that is directly coupled to the ultrasound component 220 can be eliminated. Instead, the electrical power for the ultrasound component 220 can be provided with electrical cable 202 and a slidable electrical contact (not shown) between handle 102 and the ultrasound component 220 can deliver current to the piezoelectric elements 225.

As can be seen in FIGS. 1, 2A-2B, and 4, the resecting device 10 may be part of a system that includes a negative pressure source 240 operatively coupled to a tissue extraction channel 252 in the device which is in part the passageway in the inner sleeve 125. As can be understood from FIGS. 1 and 2A, a flexible outflow tube 254 can extend from the negative pressure source 240 to a quick-connect fitting 255 at the end of the fixed member 165. The tissue extraction channel 252 extends through inner sleeve 125 and handle 102 to the cylindrical fixed member 165 (FIG. 2A). In one variation, the negative pressure source 240 is a peristaltic pump but any other source such as hospital wall suction may be used. In another variation, the extraction channel 252 in the combination of inner sleeve 125 and fixed member 165 can transition from a smaller cross-section to a larger cross-section to facilitate the extraction of cut tissue chips. The controller 210 is adapted to control the negative pressure source 240 as indicated in FIG. 1. A tissue catch structure 258 is provided in outflow tube 254 to collect tissue chips.

In FIGS. 1, 2A-2B, and 4, it can be seen that the resecting device 10 may be part of a system that includes a fluid source 260 that includes positive pressure mechanism for providing a pressurized fluid flow through an inflow lumen 265 in the resecting device shaft 105 which is used to assist in applying pressure to expel captured tissue chips from the instrument's working end 112. In one variation, the fluid source 260 can comprise a reservoir containing saline solution and the pressurization mechanism can be a peristaltic pump. In another variation, the fluid source can be a hospital source of an insufflation gas such as $CO_2$. The fluid is delivered by tubing 268 to the quick-connect fitting 270 in handle 102. The flow pathway 272 in the quick-connect 270 extends through tubing 275 in the handle 102 to inflow lumen 265 in the shaft portion of the resecting device 50. As can be seen in FIG. 4, the inflow lumen 265 has a small cross section, e.g., a diameter from 0.05" to 0.25", and can be formed in the wall 276 of outer sleeve 115 or can be provided in a hypotube affixed to the outer sleeve 115. In one aspect of the invention, the inflow lumen 265 extends to an outlet 277 that is proximate to or distal to the window 118 to allow a fluid flow from the outlet in the window-closed position to apply proximally-directed fluid pressure on a tissue chip (not shown) captured in the extraction channel 252. In one variation shown in FIG. 4, the inflow lumen 275 has a distal region 278 that includes a 180° turn to provide a flow from outlet 277 that is aligned with the axis 106 of the shaft 105.

Referring to FIGS. 2A-2B, the system further includes a sensor 285 in the handle that is adapted to determine the rotational position of drive member 190 and to send a signal to the controller 200 that indicates the drive member position. As can be easily understood from FIGS. 2A-2B and 4, the rotational position of drive member 190 determines the axial position of the inner sleeve and thus can indicate a fully window-open position, a window-closed position or any intermediate window-open position. In one embodiment, the sensor 285 is a Hall effect sensor that is actuated when a magnet 288 in the drive member 190 passes the sensor. In another variation, the sensor can be a mechanically-actuated switch that is actuated by an indent or projection carried by the drive member 190. In other embodiments, any sensor known it the art can be used and the sensor can be activated by either rotation of the drive member 190 or axial movement of the inner sleeve 125 in the handle 102.

Referring back to FIG. 1, the controller 210 of system 10 is adapted to receive signals from sensor 285 and in response can control operating parameters of the ultrasound transducer, the negative pressure source and the pressurized fluid source in relation to a window-open or window-closed position of the cutter. In one embodiment, a footswitch 290 is utilized to actuate the resecting device 50, but a finger-operated switch in the handle 102 also may be used (not shown). In one variation, the controller includes algorithms that activate the piezoelectric element 225 only when the inner sleeve 125 is moving forward or in distal direction from the fully window-open position to the window-closed position. In this variation, the piezoelectric element 225 is de-activated on the return or proximal stroke from the window-closed position to the window-open position. Thus, the ultrasonic or vibratory effect at the blade edge 126 of the inner sleeve 125 is only activated when tissue is being cut on the forward stroke of the inner sleeve.

Still referring to FIG. 1, the controller 210 can further control the pressurized fluid source 260 in response to signals from sensor 285 and the window-open or window-closed position of the inner sleeve 125. In one variation, the controller 210 has an algorithm that activates the fluid source 260 for a selected time interval only when the inner cutting sleeve 125 is in a fully window-closed position. Thus, at the moment the inner cutting sleeve 125 cuts and captures a tissue chip in the extraction channel 252, the controller 210 can provide a high pressure flow through the inflow lumen 275 and outlet 277 to push the tissue chip proximally in the extraction channel 252. In one embodiment, the controller 200 can have an algorithm that de-activates the motor 148 to thereby stop reciprocation of inner sleeve 125 in the window-closed position for a time interval to allow a longer pressurized flow from the fluid source 260 to push a captured tissue chip through the extraction lumen 252. For example, the inner sleeve 125 may be stopped for a time interval ranging from 0.1 second to 2 seconds.

Figure 5:
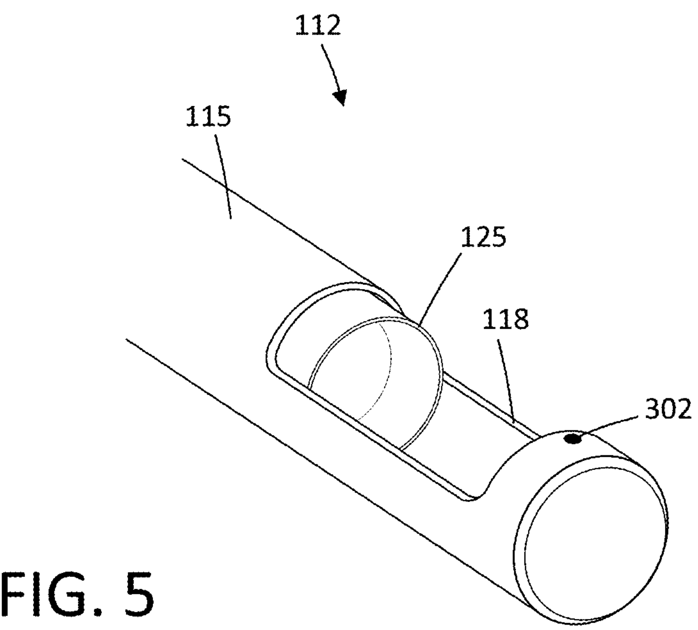
FIG. 5 is a perspective view of the working end of a resecting device showing a sensor for sensing tissue contact.
Figure 6:
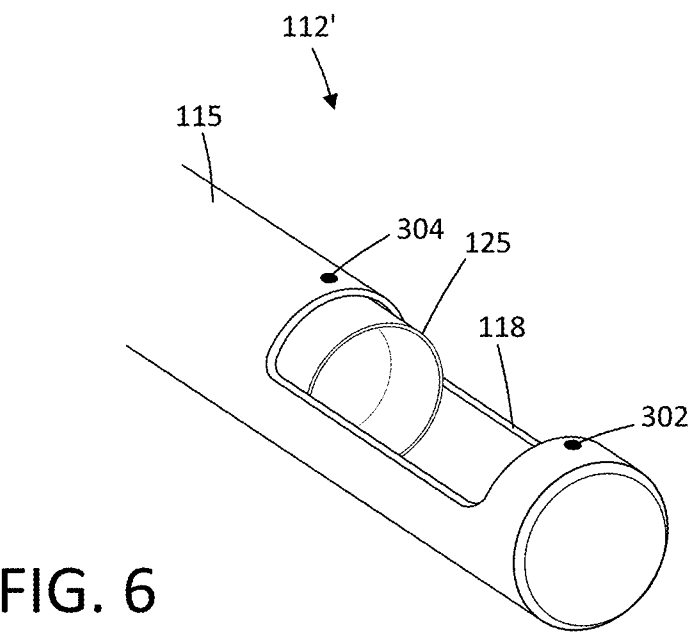
FIG. 6 is a perspective view of another working end of a resecting device showing a plurality of sensors for sensing tissue contact.

Referring to FIG. 1, the controller 210 can include algorithms to modulate the negative pressure source 240 in response to signals from a sensor and the corresponding window-open or window-closed condition of the resecting device. In one variation of working end 112 shown in FIG. 5, the at least one sensor 302 is provided proximate the window 118 to sense tissue contact with the window. For example, the sensor 302 can be a capacitance sensor that is configured to send a signal to the controller when the sensor contacts tissue. It can be easily understood that the capacitance reading from the sensor 302 when in contact with tissue would differ greatly from a capacitance reading in the absence of tissue contact. Any similar type sensor 302 could be used, such as an impedance sensor, pressure sensor and the like. As can be seen in FIG. 6, another variation of working end 212' can have a plurality of sensors 302 and 304 and can be used to modulate the negative pressure source 240. In one variation, the controller 210 can activate the negative pressure source 240 only when a sensor 302 and/or 304 (FIGS. 5 and 6) is in contact with tissue which then provides suction force to suction tissue into the window 118. At other times, for example when the physician is re-positioning the working end relative to tissue targeted for resection, the negative pressure source 240 would be de-activated to thus prevent insufflation gas from being withdrawn from the working space 55 (see FIG. 1).

In another aspect of the invention, the controller 210 can include an algorithm adapted to move the inner cutting sleeve 125 to a predetermined position relative to the window 118 each time the physician de-activates the device. In one variation, when the physician lifts his or foot from the footswitch, or lifts finger from a trigger, a "stop-reciprocation" signal is sent to controller 210 which in turn determines the location of the inner sleeve 125 relative to the window 118 by means of a timer and the next signal (or previous signal) from the position sensor 285 that determines the rotational position of drive member 190. The controller 210 then can calculate the time interval needed to stop the drive member 190 and sleeve 125 at a predetermined location based on a library of known time intervals following de-activation of the motor 148 to allow the inner sleeve 125 to coast (overcome momentum) to the predetermined position. In one embodiment, the predetermined position can be a fully window-open condition, which would then allow the physician to position the open window 118 against the targeted tissue to commence resection. In one variation, the edge of window 118 and the tissue-contact sensor 302 would contact tissue which then cause the controller 210 to activate the negative pressure source 240 to suction tissue into the window and also actuate reciprocation and the piezoelectric elements 225. It should be appreciated that the controller algorithm may be programmed to activate the negative pressure source 240 and reciprocation simultaneously or the reciprocation may be actuated in a sequence, for example 0.1 seconds to 2 seconds after the negative pressure. Alternatively, the device may be provided with a two stage trigger, with a first trigger actuation movement activating the negative pressure source and an additional second trigger movement activating the reciprocation and piezoelectric element 225.

Referring back to FIGS. 3 and 4, it can be seen that the piezoelectric elements 225 are configured to cause axial motion in the distal end of the inner sleeve 125. In another variation, the piezoelectric elements can be oriented to cause rotational motion in a keyed flange 138 (see FIGS. 2A-2B) to rotationally vibrate the blade edge 126 of the inner sleeve. In another variation, a plurality of piezoelectric elements can be provided to cause both axial and rotational motion in the distal end of the inner sleeve. Such motion can be sequential or contemporaneous. The blade edge 126 can have any suitable configuration such as being smooth or having teeth, etc.

Figure 7:
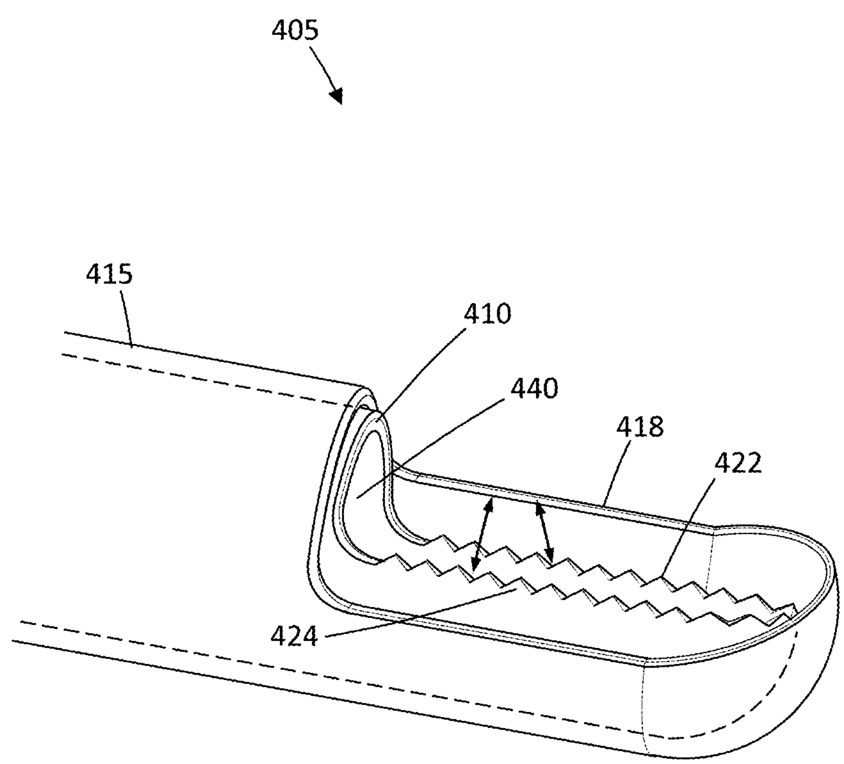
FIG. 7 is a perspective view of another working end of a resecting device showing a rotating inner sleeve that can be coupled to an ultrasound source.

FIG. 7 illustrates another variation of a working end 405 corresponding to the invention in which an inner sleeve 410 is configured to rotate relative to outer sleeve 415 rather that reciprocating as in the embodiment of FIGS. 1-5. It can be easily understood that a handle similar to that of FIG. 2A can use an appropriately geared motor to rotate the inner sleeve 415 at a selected speed or rotate the sleeve 415 sequentially in clockwise and counter-clockwise directions. Contemporaneously, the at least one piezoelectric element can be used to vibrate the inner sleeve 415 in the manner described previously. As can be seen in FIG. 7, the window 418 of inner sleeve 415 has sharp teeth 422 at its edge 424, and the combination of rotation and ultrasonic or vibratory movement of edge 424 will assist is cutting or sawing tougher tissues. In one variation, the controller can include an algorithm that will sequentially rotate the inner sleeve from a window-open start position in clockwise direction from 5° to 30°, then back past the start position and then 5° to 30°, in a counter-clockwise direction followed by one or more increased sequential angular rotation to cut a tissue chip. After successive cutting by such sequential rotations, the inner sleeve 415 can be rotated to the fully window closed position to capture the tissue in the extraction lumen 440 of the inner sleeve. In one variation, an inflow channel 265 as shown in FIG. 4 can be provided in the device of FIG. 7 to allow proximally directed fluid flow to push the tissue chip in the proximal direction in the extraction channel.

In general, the controller 210 can control all operating parameters of the ultrasound component, the motor drive that reciprocates or rotates the inner sleeve, the negative pressure source and the pressurized fluid source, as well as responding to signals from sensors to provide sequential actuation of different component as well as to provide interlocks between various operations and functions of the resecting devices and systems of the present invention.

FIGS. 8A-8F illustrate another resecting device 500 of the invention that has a working end 512 including an outer sleeve 515 with window 518 and a reciprocating, ultrasound-actuated inner cutting sleeve 525. The resecting device 500 has at least one deformable seal 540 or valve in the tissue extraction channel 544 which allows a cut tissue chip to pass thru the seal 540. The seal 540 is configured to close to its repose state to prevent the loss of insufflation gas after tissue passes through the seal. More in particular, FIGS. 8A-8F schematically illustrate one variation of resecting device 500 and a sequence of operating the pressurized fluid source 260 and the negative pressure source 240 to assist in cutting and extraction of tissue chips in a laparoscopic procedure.

Figure 8A:
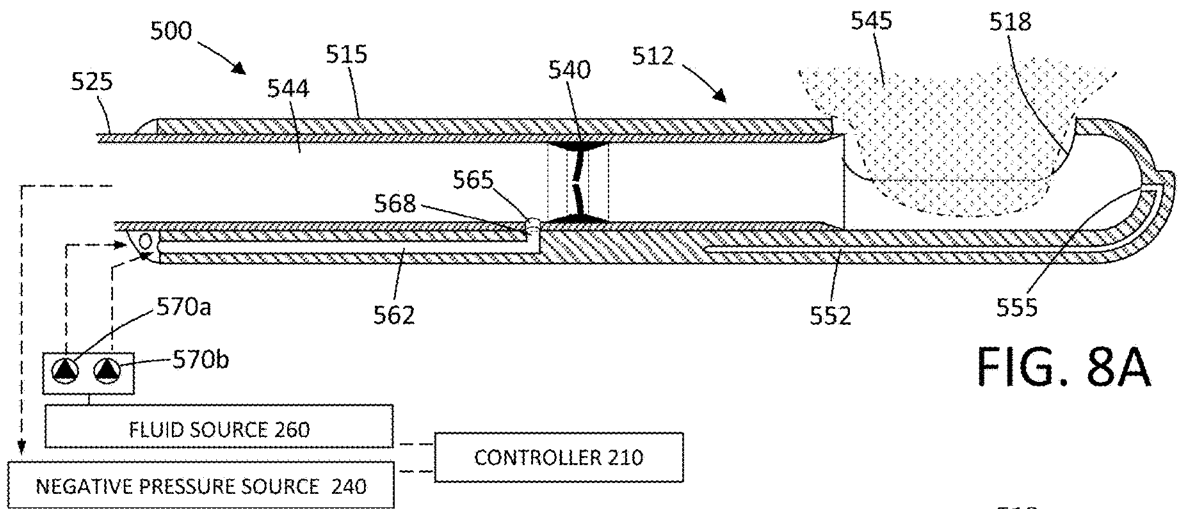
FIG. 8A is a step of a method of cutting and extracting a tissue chip in a laparoscopic resection procedure using a tubular cutter as shown in FIGS. 1-4, with FIG. 8A being a sectional view of a resecting device working end illustrating the activation of a negative pressure source to suction tissue into a window of the cutter.
Figure 8B:
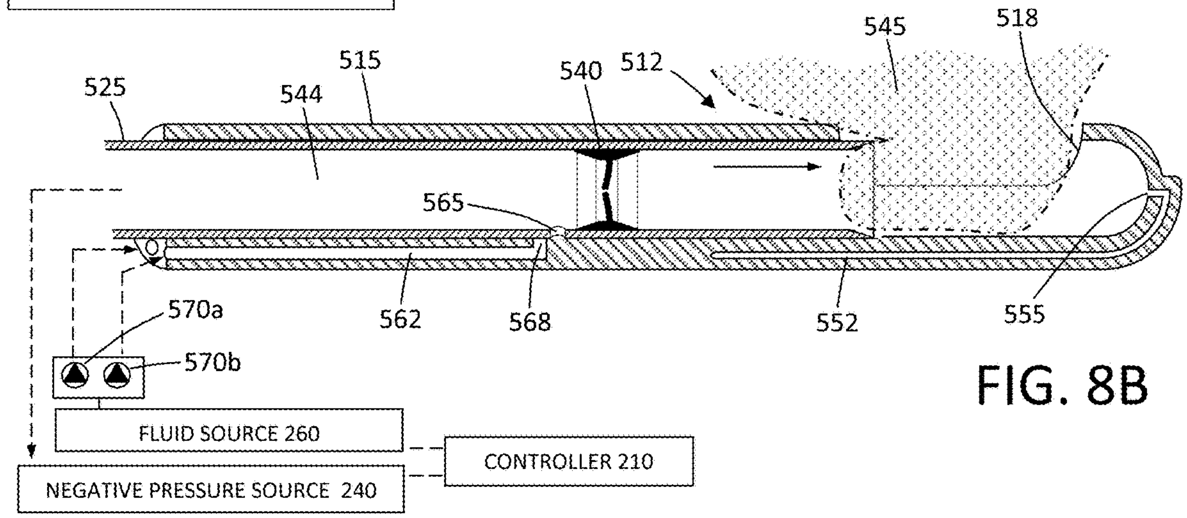
FIG. 8B is another step of the method following the step of FIG. 8A illustrating the activation of motor drive to reciprocate the inner cutting sleeve and actuating an ultrasound component to provide vibratory motion at the inner sleeve edge to resect tissue drawn into the window of the cutter.
Figure 8C:
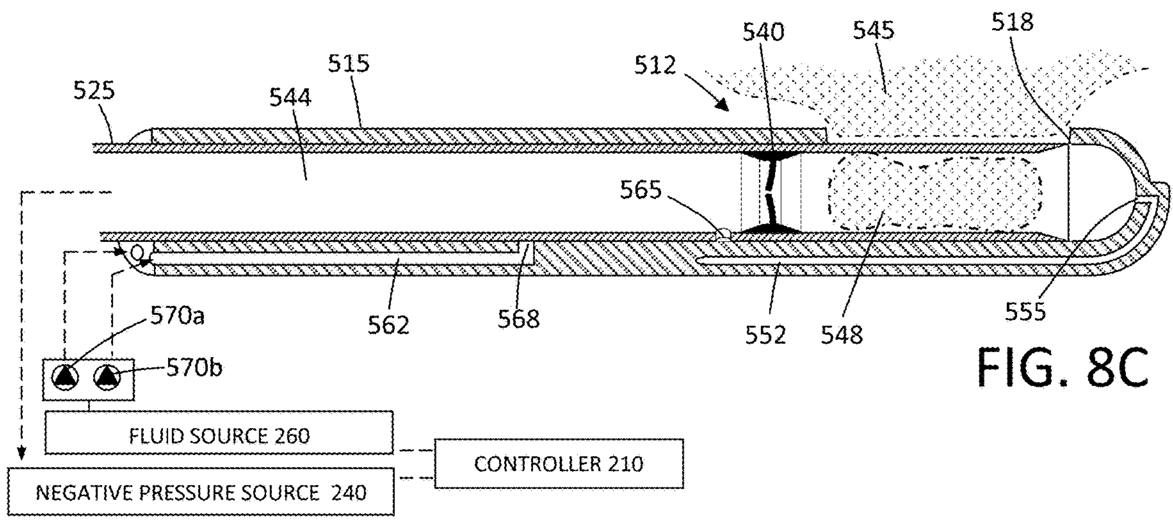
FIG. 8C is another step following the step of FIG. 8B illustrating a resected tissue chip captured in an interior passageway of the cutting sleeve.

In FIG. 8A, the working end 512 of the resecting device is positioned so that the window 518 is in contact with a targeted tissue volume 545. As described above, the controller 210 has algorithms that stop the inner sleeve in a window-open position of FIG. 8A. At this point in time, none of the operational mechanisms (ultrasound component, motor drive, negative pressure source and pressurized fluid source) are activated, thus no insufflation gas is lost though the device. The insufflation pressure is maintained automatically by an independent insufflator system as is known in the art. In one variation, the physician then partially actuates a trigger switch 290 (see FIG. 1) which signals the controller 210 to activate the negative pressure source 240. In FIG. 8A, the negative pressure source thus suctions a portion of the targeted tissue 545 into the window 518. In FIG. 8B, the physician further actuates the trigger switch 290 which maintains activation of the negative pressure source 240 and activates the motor 148 (FIG. 2B) to cause reciprocation of the inner sleeve 525 and simultaneously activates the ultrasound component. As can be seen in FIG. 8B, the distal movement of the inner sleeve 525 begins to cut tissue. FIG. 8C illustrates the inner sleeve 525 at the distal end of its stroke which captures a tissue chip 548 in the extraction channel 544 of the inner sleeve.

Figure 8D:
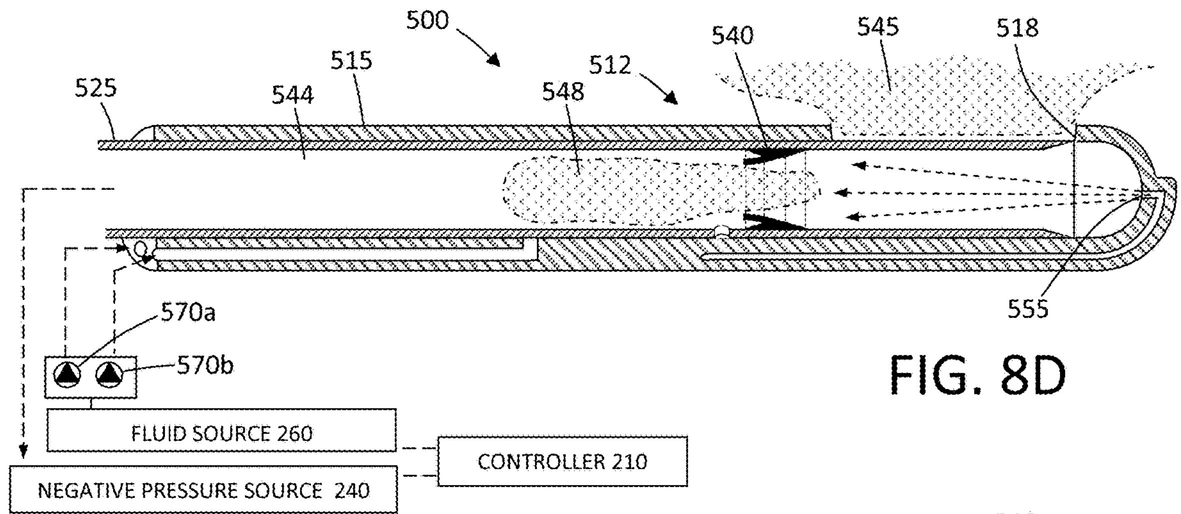
FIG. 8D is another step depicting actuation of a pressurized fluid flow through an inflow channel and outward from a flow outlet distal to an interior seal to eject the tissue chip through the seal in a proximal direction in the interior passageway of the inner sleeve.
Figure 8E:
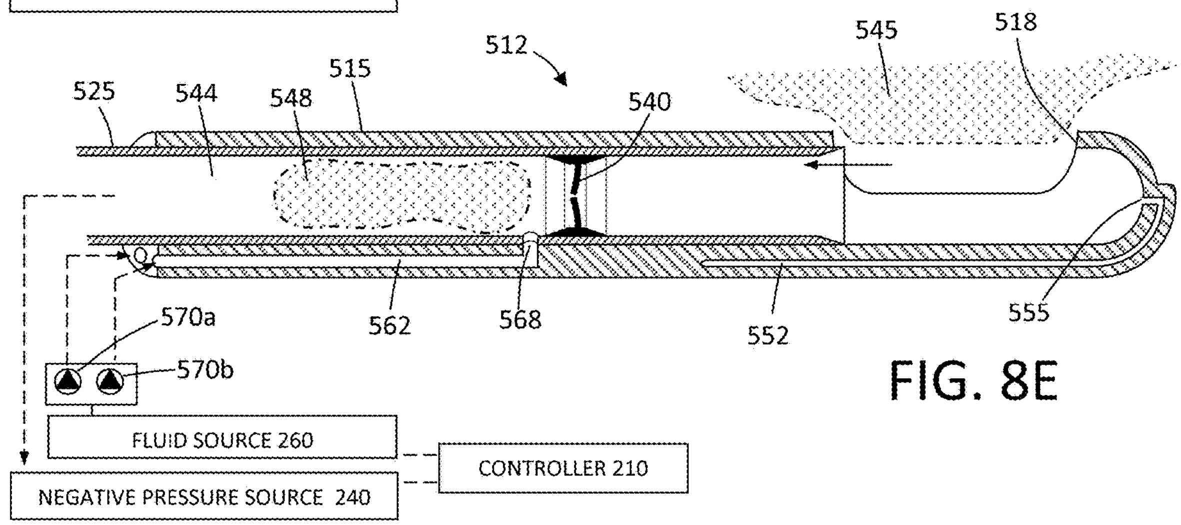
FIG. 8E is a further step after the pressurized fluid flow of FIG. 8D pushes the tissue chip through the seal in the interior passageway.

In FIG. 8D, the position of inner sleeve 525 at the distal end of its stroke can cause a controller algorithm to optionally terminate the ultrasound component and optionally halt reciprocation for a brief interval as described above. With the inner sleeve 525 in the window closed position in FIG. 8D, the controller 210 causes the fluid source 260 to provide a high pressure fluid flow through first inflow channel 552 and outward from outlet 555 to thus push the tissue chip 548 through the seal 540 in extraction channel 544 as depicted in FIG. 8E. The controller 210 can control the fluid volume, pressure and duration of the flow to optimize the expulsion of the tissue chip through the seal 540. An instant after the fluid flow has applied proximally-directed forces to the tissue chip, FIG. 8E shows the controller has activated the motor 148 to thereby move the inner sleeve 525 to the window open position.

Figure 8F:
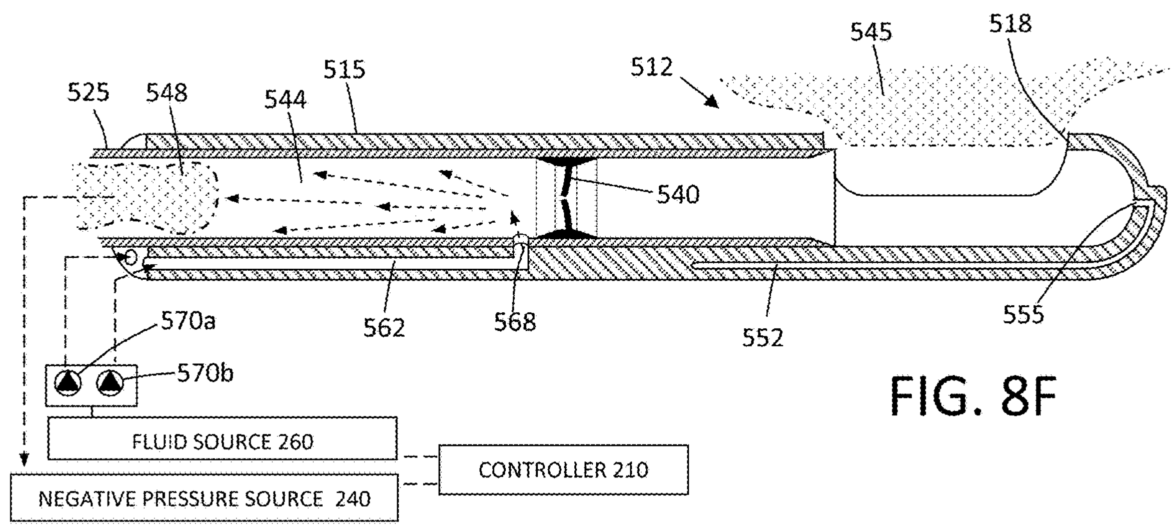
FIG. 8F depicts a further step of the invention wherein another pressurized fluid flow outward from an outlet proximal of the seal to pushes the tissue chip further in the proximal direction in the interior passageway.

FIG. 8F illustrates another step in the sequence of resecting tissue wherein the controller 210 causes the fluid source 260 to provide another high pressure fluid flow through a second inflow channel 562 and outward from outlet 565 to push tissue chip 548 further outward (proximally) through the extraction channel 544. It can be seen that the inflow channel 562 is within wall of outer sleeve 515 which has an outlet 568 that is aligned with port 565 in the inner sleeve 525 to thus permit a high pressure flow to reach the extraction channel 544 in the inner sleeve. In order to provide the fluid flows sequentially through the first inflow channel 552 and then the second inflow channel 562, the controller 210 can control solenoid valves 570*a* and 570*b* as shown schematically in FIGS. 8A-8F. Following the step of using the fluid flow to expel tissue as depicted in FIG. 8F, the sequence of steps 8A-8F can automatically be repeated to rapidly resect the targeted tissue volume. It should be appreciated that the inner sleeve 525 may reciprocate at a constant rate and the controller 210 can actuate the fluid source 260 at selected intervals to provide the sequential fluid flows through the first and second inflow channels 552 and 562. Further, the system can be configured to cause the pressurized fluid flow through the second inflow channel 562 with the inner sleeve 525 in any axial position relative to window 518.

Figure 9:
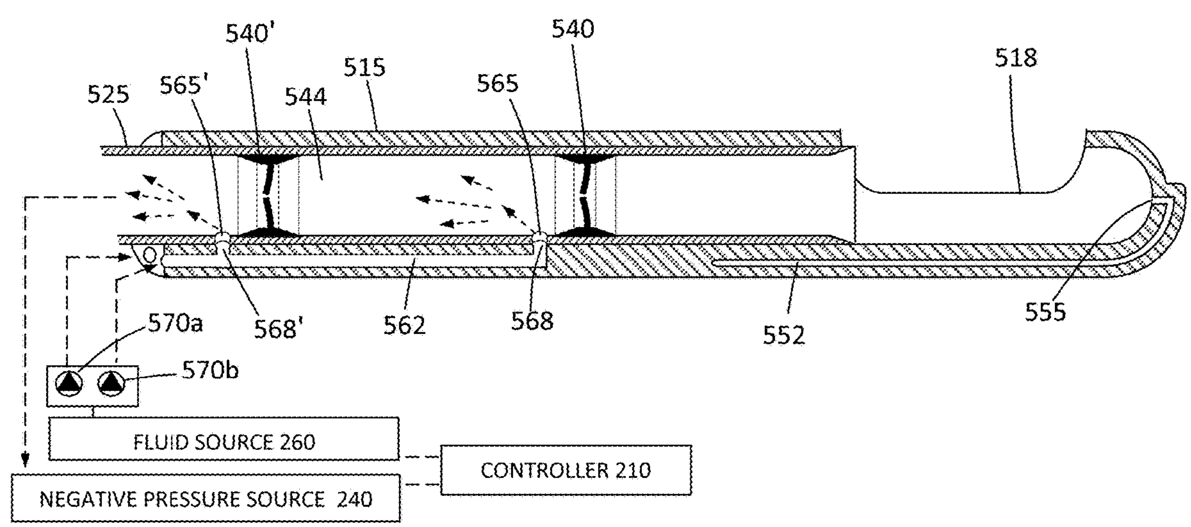
FIG. 9 is a perspective view of another working end of a resecting device showing a plurality of seals in the tissue extraction lumen and flow outlets for providing independent fluid flows distal of each seal to assist in expelling tissue through each seal.

In another variation, referring to FIG. 9, the inner sleeve 525 may be configured with a plurality of seals, for example seals 540 and 540' with inflow ports 565 and 565' (which can be elongated slots) to allow for a plurality of flow pulses in different axial locations to push and expel tissue chips through the extraction channel 544. The flow pulses can be contemporaneous or sequential through inflow ports 565 and 565' from a single inflow channel 562 and outlets 568 and 568' or can be sequenced through a plurality of independent inflow channels each in communication with an inflow ports 565 and 565'. In various embodiments, the number of seals 540 and corresponding inflow ports 565 can range from 1 to 10.

In any embodiment, the passageway seal 540 can be any type of flexible leaflet-type seal, hinged-door seal, duckbill-type seal or the like that is adapted to close the passageway in a repose condition.

Figure 10:
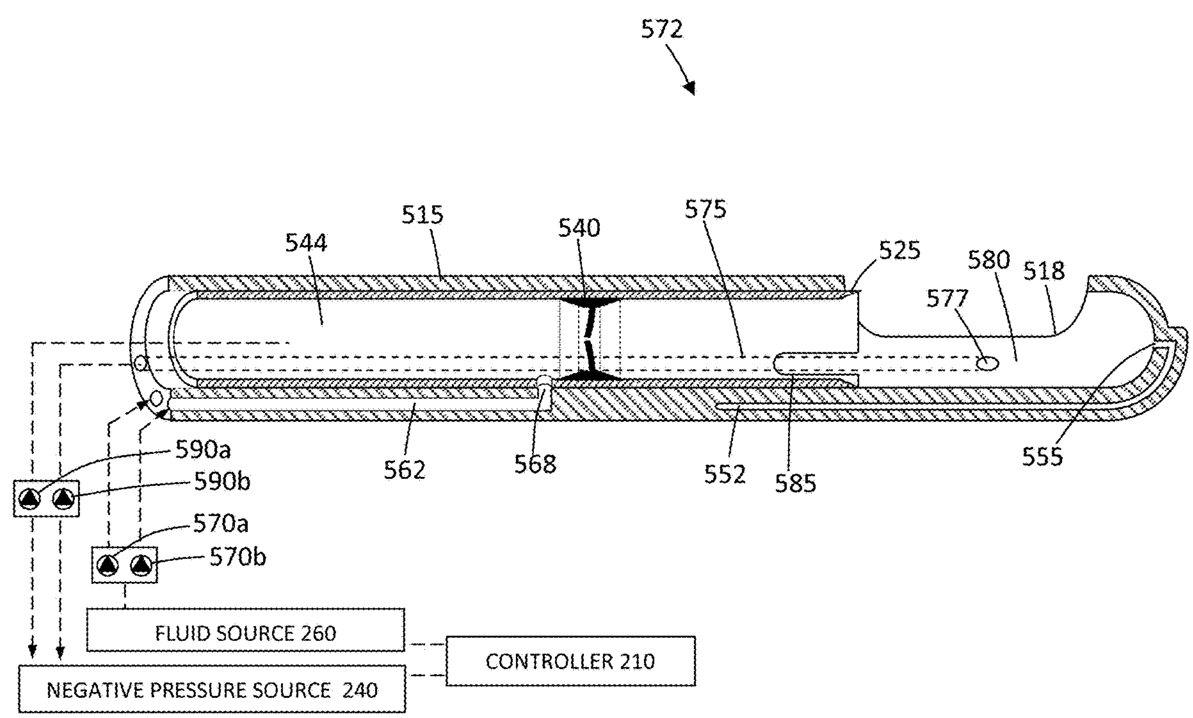
FIG. 10 is a perspective view of another resecting device working end showing an independent fluid channel with a port proximate the window in the outer sleeve for suctioning tissue into the window.

FIG. 10 illustrates another resecting device 570 that is similar to that of FIGS. 8A-8F except that outer sleeve 515 carries an independent passageway 575 coupled to negative pressure source 240 that is controlled independently by controller 210 to provide suction forces in the interior of window 518. More in particular, the independent passageway 575 in outer sleeve 515 extends to a distal opening 577 in a distal region of the bore 580 of sleeve 515 proximate window 518. Thus, the controller 210 can actuates the negative pressure source 240 to suction tissue into the window independent of suction force provided through the tissue extraction channel 544 of the inner sleeve 525. Further, the controller 210 can use an algorithm to modulate suction pressure through passageway 575 and opening 577 during different portions of the stroke of the inner sleeve 515 to optimize suction for pulling tissue into the window and to minimize loss of insufflation gas. The controller 210 can operate solenoid valves 590*a* and 590*b* to control negative pressure in the channels 544 and 575. In one variation, the inner sleeve 515 can have a slot or notch 585 that is axially aligned with opening 577 so that the opening is not covered by the inner sleeve 515 during a distal region of the sleeve's reciprocation. Thus, suction forces can be applied to tissue throughout reciprocation of the inner sleeve 515.

In the various embodiments described above, the inflows from fluid source have been described as any suitable fluid or flow media. It should be appreciated the flow media can be a liquid (e.g., saline or sorbital) or a gas such as $CO_2$. Either a liquid or gas can be used to assist in expelling tissue, with each having its advantages. The use of a incompressible liquid could apply greater expelling forces to a captured tissue chip. The use of an insufflation gas can reduce the complexity of the system. In a variation, the system could use a gas media to expel a just-cut tissue chip from the region of the window through the seal 540 in the step shown in FIG. 8D and then use a liquid flow in the step depicted in FIG. 8F. In such a variation, pulse liquid flows can operate continuously or intermittently during operation of the device.

It should be appreciated that the features described in the system embodiments of FIGS. 8A-10 including seals 540 and independent suction passageway 570 can be provided in a "rotating" inner cutting sleeve as illustrated in FIG. 7.

In another variation, a plurality of piezoelectric element can each be coupled to a separate elongated member or component that is a part of an assembly that comprises the reciprocating or rotating cutting sleeve. Thus each piezoelectric element can drive a member that has a selected length to cooperate with a standing wave in the material caused by the piezoelectric element to optimize the tissue effect at the distal end of the cutting sleeve. Each elongated member can have an axial or spiral configuration.

Although particular embodiments of the present invention have been described above in detail, it will be understood that this description is merely for purposes of illustration and the above description of the invention is not exhaustive. Specific features of the invention are shown in some drawings and not in others, and this is for convenience only and any feature may be combined with another in accordance with the invention. A number of variations and alternatives will be apparent to one having ordinary skills in the art. Such alternatives and variations are intended to be included within the scope of the claims. Particular features that are presented in dependent claims can be combined and fall within the scope of the invention. The invention also encompasses embodiments as if dependent claims were alternatively written in a multiple dependent claim format with reference to other independent claims.

What is claimed is:

1. A method for cutting tissue, said method comprising:
providing a cutting sleeve;
actuating a first ultrasound transducer operatively coupled to the cutting sleeve to cause at least one of axial and rotational oscillatory motion in a distal end of the cutting sleeve;
advancing the distal end of the cutting sleeve through tissue to cut said tissue; and
actuating a second ultrasound transducer operatively coupled to the cutting sleeve to cause the other of axial and rotational oscillatory motion in the distal end of the cutting sleeve.

2. The method of claim 1 wherein advancing the cutter sleeve comprises reciprocating said sleeve.

3. The method of claim 2 wherein advancing the cutter sleeve further comprises rotating the cutter sleeve.

4. The method of claim 3 wherein the cutting sleeve is reciprocated and rotated within an outer sleeve past a window in the outer sleeve, wherein the tissue to be cut has been drawn into the window by a negative pressure.

5. The method of claim 4 wherein the negative pressure extracts tissue through a lumen in the cutting sleeve.

6. The method of claim 4 wherein the cutting sleeve is reciprocated at a reciprocation rate between 1 and 10 Hz.

7. The method of claim 4 wherein reciprocating and/or rotating the cutting sleeve comprises driving the sleeve with a motor drive.

8. The method of claim 7 further comprising controlling operating parameters of the ultrasound transducer(s), the motor drive, the negative pressure source with a controller.

9. The method of claim 8 further comprising sending signals from sensors to the controller indicating a position of the cutting sleeve relative to the window in the outer sleeve.

10. The method of claim 9 wherein the controller modulates activation of the ultrasound transducer(s) in response to the sensor signals that indicate the position of the inner sleeve.

11. The method of claim 10 wherein the controller activates the ultrasound transducer when the cutting sleeve moves toward a window-closed position to cut tissue and de-activates the ultrasound transducer when the cutting sleeve moves toward a window-open position.

12. The method of claim 8 wherein the controller activates a pressurized fluid source when the inner sleeve is in a window-closed position.

13. The method of claim 12 wherein the controller de-activates the pressurized fluid source when the inner sleeve is in a window-open position.

14. The method of claim 12 wherein the pressurized fluid source comprises a liquid source.

15. The method of claim 12 wherein the pressurized fluid source comprises a gas source.

16. A method for cutting tissue, said method comprising:
providing a cutting sleeve;
actuating a first ultrasound transducer operatively coupled to the cutting sleeve to cause at least one of axial and rotational oscillatory motion in a distal end of the cutting sleeve; and
advancing the distal end of the cutting sleeve through tissue to cut said tissue;
wherein advancing the cutter sleeve comprises reciprocating and rotating said sleeve within an outer sleeve past a window in the outer sleeve, wherein the tissue to be cut has been drawn into the window by a negative pressure.

17. The method of claim 16 further comprising actuating a second ultrasound transducer operatively coupled to the cutting sleeve to cause the other of axial and rotational oscillatory motion in the distal end of the cutting sleeve.

18. The method of claim 16 wherein the negative pressure extracts tissue through a lumen in the cutting sleeve.

19. The method of claim 16 wherein the cutting sleeve is reciprocated at a reciprocation rate between 1 and 10 Hz.

20. The method of claim 16 wherein reciprocating and/or rotating the cutting sleeve comprises driving the sleeve with a motor drive.

21. The method of claim 20 further comprising controlling operating parameters of the ultrasound transducer(s), the motor drive, the negative pressure source with a controller.

22. The method of claim 21 further comprising sending signals from sensors to the controller indicating a position of the cutting sleeve relative to the window in the outer sleeve.

23. The method of claim 22 wherein the controller modulates activation of the ultrasound transducer(s) in response to the sensor signals that indicate the position of the inner sleeve.

24. The method of claim 23 wherein the controller activates the ultrasound transducer when the cutting sleeve moves toward a window-closed position to cut tissue and de-activates the ultrasound transducer when the cutting sleeve moves toward a window-open position.

25. The method of claim 21 wherein the controller activates a pressurized fluid source when the inner sleeve is in a window-closed position.

26. The method of claim 25 wherein the controller de-activates the pressurized fluid source when the inner sleeve is in a window-open position.

27. The method of claim 25 wherein the pressurized fluid source comprises a liquid source.

28. The method of claim 25 wherein the pressurized fluid source comprises a gas source.

* * * * *